United States Patent
Mura et al.

(10) Patent No.: US 11,466,304 B2
(45) Date of Patent: Oct. 11, 2022

(54) SYSTEM FOR EXPOSURE TO A PRODUCT IN THE FORM OF AN AEROSOL AND METHOD FOR EVALUATING THE INTEGRITY OF A CONTAINER BY MEANS OF SUCH A SYSTEM

(71) Applicant: CONFARMA FRANCE, Hombourg (FR)

(72) Inventors: Alexandre Mura, St Amarin (FR); Anja Fritsch, Schliengen (DE)

(73) Assignee: CONFARMA FRANCE, Hombourg (FR)

( * ) Notice: Subject to any disclaimer, the term of this patent is extended or adjusted under 35 U.S.C. 154(b) by 0 days.

(21) Appl. No.: 16/965,309

(22) PCT Filed: Jan. 28, 2019

(86) PCT No.: PCT/EP2019/051971
§ 371 (c)(1),
(2) Date: Jul. 28, 2020

(87) PCT Pub. No.: WO2019/145525
PCT Pub. Date: Aug. 1, 2019

(65) Prior Publication Data
US 2021/0115492 A1 Apr. 22, 2021

(30) Foreign Application Priority Data

Jan. 29, 2018 (FR) ........................................ 1850661
Jan. 29, 2018 (FR) ........................................ 1850663

(51) Int. Cl.
*C12Q 1/18* (2006.01)
*C12Q 1/22* (2006.01)
(Continued)

(52) U.S. Cl.
CPC .................. *C12Q 1/22* (2013.01); *A61L 2/28* (2013.01); *B01J 13/0095* (2013.01);
(Continued)

(58) Field of Classification Search
CPC ...... A61L 2/00; A61L 2/26; A61L 2/28; B01J 13/00; B01J 13/0095; B01J 19/00;
(Continued)

(56) References Cited

U.S. PATENT DOCUMENTS 9,588,105 B1 * 3/2017 Hussain ................. C12M 41/48
2016/0010047 A1   1/2016 Schmid et al.

FOREIGN PATENT DOCUMENTS

CH          323 211       7/1957
DE    10 2009 016 364   10/2010
(Continued)

OTHER PUBLICATIONS

Brossell, D. et al. 2013. A thermal precipitator for the deposition of airborne nanoparticles onto living cells—Rationale and development. Journal of aerosol science, 63, pp. 75-86. (Year: 2013).*

*Primary Examiner* — Natasha E Young
(74) *Attorney, Agent, or Firm* — Saliwanchik, Lloyd & Eisenschenk

(57) ABSTRACT

The invention relates to an aerosol product exposure system comprising an exposure chamber intended to receive an aerosol product, an aerosol product diffusion device comprising a source of aerosol product to be sprayed connected to an aerosol generator, said aerosol generator cooperating with a desiccator so as to at least partially eliminate the moisture from the aerosol product, at least one supply duct intended to bring the aerosol product into the exposure (Continued)

chamber. Such a system can in particular be used to test the integrity of a container and/or the antimicrobial activity of a product of interest.

16 Claims, 1 Drawing Sheet

(51) Int. Cl.
*A61L 2/28* (2006.01)
*G01N 33/00* (2006.01)
*B01J 13/00* (2006.01)
*B01J 19/00* (2006.01)
*B01J 19/24* (2006.01)
*B01L 1/02* (2006.01)

(52) U.S. Cl.
CPC ........ *B01J 19/0006* (2013.01); *B01J 19/0013* (2013.01); *B01J 19/0073* (2013.01); *C12Q 1/18* (2013.01); *G01N 33/00* (2013.01); *B01L 1/025* (2013.01); *G01N 2033/0081* (2013.01)

(58) Field of Classification Search
CPC ............... B01J 19/0006; B01J 19/0013; B01J 19/0053; B01J 19/0073; B01L 1/00; B01L 1/02; B01L 1/025; G01N 33/00; G01N 2033/00; G01N 2033/0078; G01N 2033/0081
See application file for complete search history.

(56) References Cited

FOREIGN PATENT DOCUMENTS

| | | |
|---|---|---|
| DE | 10 2013 005 010 | 9/2014 |
| WO | WO 2017/187008 | 11/2017 |

OTHER PUBLICATIONS

Brossell, D. et al. "A thermal precipitator for the deposition of airborne nanoparticles onto living cells—Rationale and development" *Journal of Aerosol Science*, 2013, pp. 75-86, vol. 63.

Fracchia, L. et al. "The assessment of airborne bacterial contamination in three composting plants revealed site-related biological hazard and seasonal variations" *Journal of Applied Microbiology*, 2006, pp. 973-984, vol. 100, No. 5.

O'Malley, C. A. "Device Cleaning and Infection Control in Aerosol Therapy" *Respiratory Care*, Jun. 2015, pp. 917-930, vol. 60, No. 6.

Written Opinion in International Application No. PCT/EP2019/051971, dated Feb. 28, 2019, pp. 1-11.

* cited by examiner

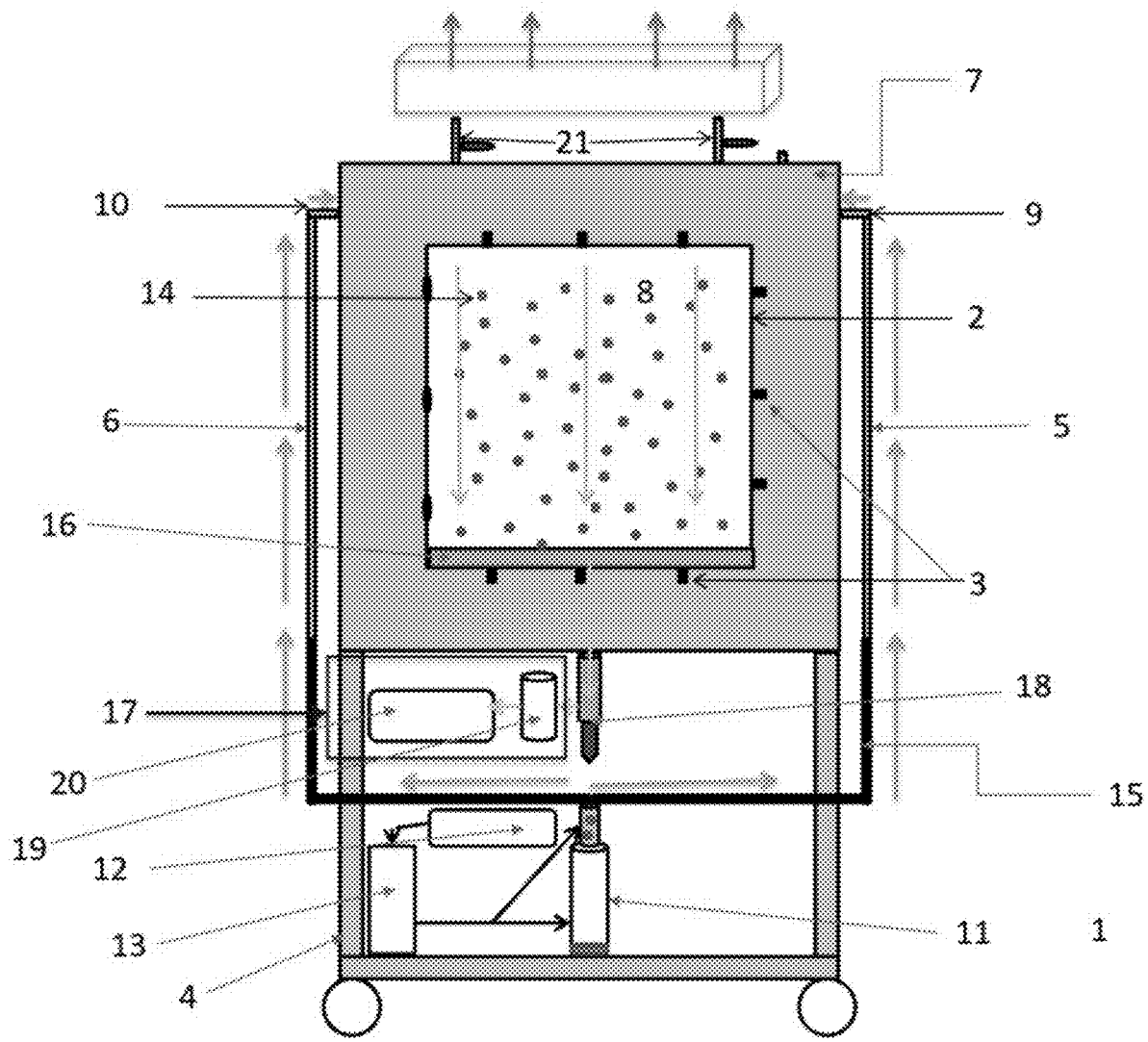

SYSTEM FOR EXPOSURE TO A PRODUCT IN THE FORM OF AN AEROSOL AND METHOD FOR EVALUATING THE INTEGRITY OF A CONTAINER BY MEANS OF SUCH A SYSTEM

CROSS-REFERENCE TO RELATED APPLICATION

This application is the U.S. national stage application of International Patent Application No. PCT/EP2019/051971, (published as WO 2019/145525), filed Jan. 28, 2019.2019, which claims priority to French Patent Application Nos. FR1850661 and FR1850663, both filed on Jan. 29, 2018.

TECHNICAL FIELD

The invention relates to a system for exposure to a product in the form of an aerosol, such as an aerosol of microorganisms. Such a system is particularly useful for testing the integrity of containers, such as packages. Therefore, the invention also concerns a process for evaluating the integrity of a container by means of such an exposure system. Such a system can also be used to evaluate the antimicrobial properties of a composition. Thus, the invention also concerns a process for evaluating the antimicrobial activity of a product of interest by means of the exposure system according to the invention.

TECHNOLOGICAL BACKGROUND

The integrity of the packages plays a key role in maintaining the sterility of the packaged products. However, the integrity failures are not necessarily detectable by the naked eye. This is the case of micro-cracks or scratches in glass containers. Other failures can be masked by a subsequent crimping operation, or on the contrary be caused by improper crimping. In the case of heat-sealed packages, the sealing areas are frequently involved. In many sectors, such as that of medical devices, pharmaceutical or food products, the integrity of the packages must be guaranteed, to maintain the sterility and quality of the products they contain throughout their shelf life, and more generally for the product and consumer safety.

Also, numerous tests for evaluating the integrity of the packages (Container Closure Integrity testing or CCIT) have been developed to allow easily verifying the areas of tightness of the packages or containers, and validating the sterility of the products they contain. In general, a CCIT method must allow evaluating the capacity of a container closure system to maintain a sterile barrier against potential contaminants, such as microorganisms, reactive gases or other harmful substances.

The Microbial Ingress test is known in particular. This test is suitable for any container containment system that can withstand ingress and pressure changes. The container to be tested is immersed in a broth containing one or several test microorganism(s), such as *Brevundimonas diminuta, Serratia marcescens, Escherichia coli*. The test can be performed in static mode, where no pressure or vacuum is applied, or in dynamic mode, where a pressure and a vacuum are applied (to simulate air transportation of the product). The main test factors are the bacterial size and motility, the differential pressure, the challenge media, the exposure time and the viable number of microorganisms in the challenge media.

The Dye Ingress Test is also widely used. In this test, the container to be tested is immersed in a dye solution (and in particular in a methylene blue solution) and pressure and vacuum are applied. The container is then inspected visually or by spectrophotometry, to observe any traces of dye in the container. The key factors for this test comprise the differential pressure, the compatibility of the dye with the product, the viscosity of the liquid and surface tension, the training and experience of the inspector (for visual inspection) and the sensitivity of the assay (spectrophotometry).

Recently, quantitative tests that do not involve the destruction of the tested samples have been developed. For example, the Mass Extraction Assay can be used to detect leaks in non-porous, rigid or flexible packages. The test is carried out by placing the container to be tested inside a test chamber which is pneumatically connected to a mass extraction leakage testing system equipped with a vacuum generator group. A predetermined vacuum level is maintained in the chamber for a predetermined period. A series of discharge cycles is performed, each cycle being intended to identify the lowest leakage rates. After each cycle, the testing system is isolated from the vacuum source and the measurements of the absolute pressure, of the pressure decay rate and/or of the gas mass flow rate are entered. Readings exceeding the predetermined limits established using negative controls indicate a leakage in the container. At the end of these leakage vacuum cycles, a final vacuum is established. The mass flow rate is measured with all the flow of the test chamber directed through the mass flow rate sensor. A mass flow rate greater than a predetermined limit established using negative controls indicates a leakage in the receptacle. However, such tests are cumbersome to implement and require expensive equipment.

There is therefore a need for means making it possible to verify the integrity of a container in order to guarantee the sterility of the product it contains, which can be easily implemented, whatever the nature of the container (flexible packages, rigid packages, syringes, etc.).

SUMMARY OF THE INVENTION

By working on these issues, the inventors have developed a device for spraying a product, such as a solution containing microorganisms, in the form of aerosol inside an enclosure, in which the container or the package to be tested has been previously placed. The form of aerosol spray allows diffusing very high concentrations of the product inside the enclosure and thus reaching an optimum concentration of said product on the surface of the container. The device according to the invention is particularly useful for carrying out microbial integrity tests. The device according to the invention indeed makes it possible to spray a microorganism solution aerosol at concentrations such that it is possible to reach concentrations of microorganisms up to $10^6 CFU/cm^2$ on the surface of the container to be tested. The device according to the invention makes it possible to test the integrity of all kinds of packages, and in particular of the flexible packages such as blood bags or the like, rigid packages such as vials, cartridges, pre-filled syringes, etc. Such a device can also be used to evaluate the anti-microbial properties of a composition. For this, it is sufficient to spray said composition in the form of aerosol in the enclosure in which a source of microorganisms has been previously placed, then to evaluate the rate of growth and/or survival of said microorganisms.

The present application therefore proposes a system for exposure to an aerosol product comprising:
- an exposure chamber;
- a device for diffusing an aerosol product comprising a source of aerosol product to be sprayed, connected to an aerosol generator, said aerosol generator cooperating with a desiccator so as to at least partially eliminate the moisture from the aerosol product; and
- at least one supply duct intended to bring the aerosol product from the diffusion device into the exposure chamber.

The application also proposes a process for evaluating the integrity of a container by means of an aerosol exposure system comprising an exposure chamber, a device for diffusing a suspension of microorganisms in the form of aerosol, comprising a source of said suspension of microorganisms connected to an aerosol generator, said aerosol generator cooperating with a desiccator so as to at least partially eliminate the moisture from the suspension of microorganisms in the form of aerosol; and at least one supply duct intended to bring the suspension of microorganisms in the form of aerosol into the exposure chamber, comprising the successive steps according to which:

(a) the container to be evaluated is introduced into the exposure chamber;

(b) an aerosol is generated from the suspension of microorganisms, said aerosol being vaporized in the exposure chamber such that the microorganisms are in contact with the container;

(c) the container is recovered and optionally incubated under conditions allowing the growth of the microorganisms in the suspension of microorganisms;

(d) the possible presence of microorganisms is detected inside the container.

The application also proposes a process for evaluating the antimicrobial activity of a product of interest by means of an aerosol exposure system comprising an exposure chamber, a device for diffusing the aerosol product of interest comprising a source of the product of interest connected to an aerosol generator, said aerosol generator cooperating with a desiccator so as to at least partially eliminate the moisture from the aerosol product of interest; and at least one supply duct intended to bring the aerosol product of interest into the exposure chamber, the process comprising the steps according to which:

(a) a source of microorganisms is introduced into the exposure chamber;

(b) an aerosol is generated from the product of interest, said aerosol being vaporized in the exposure chamber such that the microorganisms are in contact with said product of interest;

(c) the microorganisms are recovered;

(d) the rate of growth and/or survival of the microorganisms is evaluated.

The invention also relates to the use of the aerosol exposure system according to the invention for testing the integrity of a package and/or the antimicrobial activity of a product of interest.

BRIEF DESCRIPTION OF THE FIGURE

FIG. 1 schematically represents an aerosol exposure system according to an exemplary embodiment of the invention.

DETAILED DESCRIPTION

The inventors have succeeded in developing an aerosol product exposure system, wherein the moisture of the product is at least partially reduced before it is sprayed into the exposure chamber.

The aerosol product exposure system according to the invention is mainly characterized by (i) an exposure chamber, intended to receive an aerosol product and the container to be tested or a source of microorganisms, (ii) an aerosol diffusion device, comprising a source of aerosol product to be sprayed, connected to an aerosol generator which cooperates with a desiccator and (iii) one or several supply duct(s) intended to bring the aerosol into the exposure chamber.

According to the invention, "aerosol" means a stable suspension of solid or liquid particles in a gas.

Surprisingly, the inventors have discovered that the at least partial elimination of the moisture from the aerosol product to be sprayed before it is sprayed inside the exposure chamber, or enclosure, allows concentrating the product to be sprayed. Thus, in the case of a suspension of microorganisms, the desiccation allows spraying high concentrations of microorganisms and thus easily reaching a concentration on the surface of a container placed inside the exposure chamber of $10^6 CFU/m^2$. In one particular embodiment, the aerosol product is a spore suspension. In another embodiment, the aerosol product is a composition whose antimicrobial activity must be tested.

Any means allowing the creation of an aerosol can be used as an aerosol generator. In one embodiment, the aerosol generator comprises a receptacle (containing the product to be sprayed) pressurized by means of a propellant gas. Those skilled in the art are able to choose the most suitable aerosol generator, depending in particular on the product to be sprayed.

Likewise, any desiccator making it possible to at least partially eliminate the moisture from a composition or suspension can be used. In one embodiment, the desiccant of the desiccator is dry air. In another embodiment, the desiccant of the desiccator is a hydrophilic compound, such as silica gel. Those skilled in the art are able to choose the most suitable desiccator, in particular according to the product to be sprayed.

According to the invention, the desiccator is advantageously able to eliminate at least 50% of the moisture initially contained in the product to be sprayed, more preferably at least 60%, 70%, 75%, 80%, 85% or more. Advantageously, the sprayed aerosol product has a moisture content of less than 50%.

According to the invention, the aerosol product exposure system comprises one or several duct(s) intended to bring the aerosol product from the diffusion device into the exposure chamber. Advantageously, the exposure system comprises two ducts, opening out on either side into the volume of the exposure chamber, in order to uniformly distribute the aerosol throughout the exposure chamber. In one embodiment, the supply duct(s) open out into the upper portion of the exposure chamber, so as to bring the aerosol product into the upper portion of said chamber. Thus, the product sprayed inside the exposure chamber will fill the entire volume of said chamber by gradually falling by sedimentation.

Within the context of the invention, the "high" portion designates the considered portion of the element that is the most distant from the surface on which said element rests, as opposed to the "low" portion.

Advantageously, the system according to the invention also comprises discharge means, able to discharge the sprayed product out of the exposure chamber at the end of the test. For example, the discharge means comprise a discharge valve, disposed in the lower portion of the exposure chamber, and at least one filter able to receive the product at the end of the discharge valve. Thus, when the aerosol product falls by sedimentation, it is received in the lower portion by said discharge means. In a particular embodiment, the discharge means comprise an air filter and/or an activated carbon filter. The filter advantageously allows retaining the microorganisms in the case where the sprayed product is a suspension of microorganisms. The presence of at least one filter allows in particular maintaining an atmospheric pressure in the exposure chamber while preventing the exit of the microorganisms outside the chamber, thereby preventing the contamination of the surrounding air. The discharge means comprising at least one filter particularly allow avoiding overpressure in the chamber while retaining the microorganisms, thus maintaining an optimal concentration of the particles sprayed in the exposure chamber.

In one particular embodiment, at least one filter is disposed in the lower portion of the exposure chamber. This allows in particular retaining in the exposure chamber the particles, particularly the microorganisms, that have sedimented.

In one particular embodiment, the discharge means comprising at least one filter able to retain the particles are disposed in the upper portion and in the lower portion of the exposure chamber. This allows helping to maintain the exposure chamber at atmospheric pressure while maintaining the particles carried by the air as well as the particles that have sedimented inside the exposure chamber. Advantageously, the filters can be disposed in the lower portion and in the upper portion of the exposure chamber, at the inlet and/or at the outlet of the discharge valve.

In one particular embodiment, the exposure chamber is an enclosure able to be hermetically closed. Any means making it possible to guarantee the tightness of an enclosure can be used, and in particular seals, mechanical toggle clamps, etc.

In one particular embodiment, the system according to the invention comprises air supply means, disposed in the upper portion of the diffusion chamber.

Advantageously, the aerosol exposure system according to the invention also comprises means for controlling, and optionally adjusting, at least one parameter among the pressure, the temperature and the hygrometry inside the exposure chamber. Indeed, according to the tests carried out, it can be useful, even necessary, to control the temperature, the pressure, the moisture, etc., in order to be able to possibly adjust them. For example, it may be necessary to maintain constant pressure and temperature previously determined when the integrity of a container is tested, in particular to simulate air transportation conditions. In one embodiment, these control means comprise one or several sensor(s) disposed inside the exposure chamber. Such control means are conventionally used by those skilled in the art, who will be able to choose the most suitable ones based on the parameter(s) to be controlled and possibly to be adjusted.

The aerosol exposure system comprises advantageously means for maintaining a sample in the exposure chamber, in order to maintain the container to be tested or the test microorganism sample during the implementation of a process for evaluating the integrity of a container or a process for evaluating the antimicrobial activity of a product of interest. In one embodiment, such maintaining means consist of a plate on which the container or the sample of microorganisms to be tested can be placed. In another embodiment, the maintaining means are means that allow maintaining the container to be tested in suspension inside the exposure chamber. Such suspension maintaining means promote the deposition of the aerosol over the entire surface of said container. It is in particular possible to use a rod or cord at the end of which the container to be tested will be suspended.

According to the invention, such a system can advantageously be used to implement a process for evaluating the integrity of a container, in which the source of aerosol product to be sprayed is a suspension of microorganisms, said process successively comprising the steps according to which:

the container to be evaluated is introduced into the exposure chamber;

an aerosol is generated from the suspension of microorganisms, said aerosol being vaporized in the exposure chamber such that the microorganisms are in contact with the package;

optionally, air is injected into the exposure chamber so as to remove the microorganisms from said exposure chamber;

the container is recovered and optionally incubated under conditions allowing the growth of microorganisms in the suspension of microorganisms;

the possible presence of microorganisms is detected inside the container.

Within this context, the presence of microorganisms is systematically sought after recovery of the container on which the aerosol product, particularly the suspension of microorganisms, has been sprayed.

According to the invention, the container designates any packaging, supposed to be hermetically closed, that allows containing a liquid, solid or gaseous product. Such a container can in particular be a flexible pouch containing a pharmaceutical product, with or without connection, a flexible or rigid package, an overpouch, a film, a sachet, etc.

Advantageously, the container and/or the exposure chamber, preferably both, have been sterilized prior to the step of depositing said container in said exposure chamber. Otherwise, it is possible to carry out an advanced disinfection or cleaning step.

The time of vaporization of the suspension of microorganisms, as well as the flow rate, can vary depending on the container to be tested, on the volume of the exposure chamber, on the initial concentration of microorganisms, etc. In particular, the vaporization time can be comprised between 5 minutes and 24 hours. Those skilled in the art are able to adapt the vaporization times and the flow rate based on these various parameters.

Advantageously, the suspension of microorganisms is vaporized in the exposure chamber so as to obtain a concentration of microorganisms on the surface of the container comprised between $10^4 CFU/cm^2$ and $10^8 CFU/cm^2$, preferably equal to $10^6 CFU/cm^2$, $+/-10^1$.

In one embodiment, the suspension of microorganisms used comprises spores. For example, the suspension comprises from $10^1$ spores/mL to $10^{12}$ spores/mL. The suspension is sprayed with a pressure comprised between 3.5 and 5 bars, for 1.5 hours$+/-30$ minutes, in an exposure chamber having a volume of 1 $m^3$, so that the entire surface of the container suspended inside said chamber is covered with microorganisms.

As indicated above, it is possible to provide a step according to which, after the step of vaporizing the suspension of microorganisms, air is injected inside the exposure chamber. Air allows expelling the microorganisms which would not have penetrated inside the container, out of the exposure chamber, to avoid in particular subsequent contaminations.

Once the container to be tested has been subjected for the desired time to the aerosol of microorganisms, said container is recovered in order to verify the possible presence of these microorganisms inside said container. According to the invention, any method for detecting microorganisms can be implemented. Those skilled in the art are able to choose both the culture conditions and the detection means to be used depending in particular on the microorganisms in the suspension of microorganisms.

The aerosol exposure system according to the invention can also be used in a process for evaluating the antimicrobial activity of a product of interest, in which the source of aerosol product to be sprayed is said product of interest, the process comprising the steps according to which:
- a source of microorganisms is disposed in the exposure chamber;
- an aerosol is generated from the product of interest, said aerosol being vaporized in the exposure chamber such that the microorganisms are in contact with said product to be evaluated;
- optionally, air is injected into the exposure chamber so as to remove said product of interest from said exposure chamber;
- the rate of growth and/or survival of the microorganisms is evaluated.

The source of microorganisms, such as a Petri dish on which bacteria are cultivated, is disposed inside the exposure chamber, so as to be in contact with the product of interest to be tested which will be sprayed in the chamber.

As indicated above, it is possible to provide for a step according to which, after the step of vaporizing the product of interest, air is injected inside the exposure chamber. Air allows expelling any trace of said product before the step of evaluating the rate of growth and/or survival of the microorganisms.

After spraying an aerosol product of interest in the exposure chamber, and optionally spraying air, the source of microorganisms is recovered, in order to evaluate the rate of growth and/or survival of said microorganisms. According to the invention, any evaluation method can be implemented. Those skilled in the art are able to choose the evaluation method to be used depending in particular on the microorganisms of the source of microorganisms.

Advantageously, during the implementation of either of the processes above, it is possible to maintain the exposure chamber at ambient temperature and/or under atmospheric pressure.

The aerosol exposure system according to the invention can therefore be advantageously used to test the integrity of a container and/or the antimicrobial activity of a product of interest.

EXAMPLES

In the following description, one exemplary embodiment of the aerosol exposure system 1 according to the invention, and as represented in FIG. 1, is described in more detail.

The aerosol exposure system 1 comprises an enclosure 2, forming an exposure chamber, which can be hermetically closed by means of mechanical toggle clamps 3 disposed all around the enclosure 2. The enclosure 2 is connected to an aerosol diffusion device 4, by two ducts 5, 6, making it possible to bring the aerosol from the diffusion device 4 to the upper portion 7 of the enclosure 2. Injection nozzles 9, 10 allow injecting the aerosol inside the enclosure 2. More specifically, the ducts 5, 6 extend on either side of the enclosure 2, so that they each open out at a different end of the enclosure 2, which allows a uniform distribution of the aerosol in the internal volume 8 of the enclosure 2. A support plate 16 is disposed in the lower portion 15 of the enclosure 2, on which a sample to be tested can be disposed. According to the invention, the sample can be a container, such as a package, or a culture of microorganisms.

The diffusion device 4 is composed in this embodiment of an aerosol generator 11, connected to a source of product to be sprayed (not represented in the FIGURE), of a compressor 12 and of a desiccant air dryer 13. Thus, the product to be sprayed is partially dried when it is put in the form of aerosol, to be diffused by means of the ducts 5, 6 in the enclosure 2. The aerosol 14 spreads throughout the volume 8 of the enclosure 2, and falls by sedimentation in the lower portion 15 of the enclosure 2.

The aerosol exposure system as represented in FIG. 1 also comprises means for discharging the aerosol 17, disposed in the lower portion 15. The discharge means 17 comprise a valve 18 through which the aerosol product is discharged, as well as a filter 19, such as a HEPA filter, connected to a blower 20.

According to the invention, it is also possible to provide for an air inlet/outlet 21. Such an air outlet, preferably located in the upper portion 7, allows in particular managing the pressure inside the enclosure 2. It can also be used at the end of the test, in order to help with the discharge of the microorganisms or of the composition vaporized inside the enclosure 2.

In the following example, the aerosol exposure system as described above was used to evaluate the integrity of flexible plastic pouches, according to the following test protocol:

The pouches were aseptically filled with sterile culture medium (caso broth type). This step was carried out under a microbiological safety station (PSM). After this filling step, a culture medium fertility test is carried out, in order to ensure the quality of the medium.

Then, the pouches, a priori closed hermetically, were placed in the exposure chamber, which was decontaminated prior to the deposition step.

Two types of pouches are deposited in the chamber:
Pouches whose integrity must be evaluated;
"Positive control" pouches (pouches showing failures made voluntarily).

The pouches are then subjected to an aerosol of *Bacillus atrophaeus* spores inside the exposure chamber.

Characteristics of the spore suspension:
Volume: 10 mL
Concentration: $5.10^{10}$ spores/mL
Characteristics of the cycle:
Duration: 1.5 h+/−0.5
Injection pressure: 3.5 bars+/−0.5 bar Disks of the same material as the pouches are disposed in the chamber in order to control by counting the actual spore concentration per $cm^2$ on the surface.

At the end of the test, the air in the enclosure is rinsed with clean air (passed through a HEPA-type filter) for 45 minutes.

The pouches are then removed from the enclosure and disposed in sterile bags and incubated between 2 days to 14 days at 32.5° C.+/−2.5° C.

The pouches with a disorder are considered as potentially positive and their positivity is confirmed after identification of the microorganism responsible for the disorder.

The invention claimed is:

1. A system for exposure to an aerosol product comprising:
    an exposure chamber for receiving an aerosol product;
    a device for diffusing an aerosol product comprising a source of aerosol product to be sprayed, connected to an aerosol generator, said aerosol generator cooperating with a desiccator so as to at least partially eliminate the moisture from the aerosol product; and
    at least one supply duct bringing the aerosol product into the exposure chamber,
    wherein the aerosol product to be sprayed is a suspension of microorganisms, a suspension of spores, or is a composition whose antimicrobial activity is to be tested.

2. The aerosol exposure system according to claim 1, wherein the supply duct is able to bring the aerosol product into the upper portion of the exposure chamber.

3. The aerosol exposure system according to claim 1, further comprising discharge means, able to discharge the product out of the exposure chamber.

4. The aerosol exposure system according to claim 3, wherein the discharge means comprise a discharge valve, disposed in the lower portion of the exposure chamber, and at least one filter able to receive the product at the end of the discharge valve.

5. The aerosol exposure system according to claim 4, wherein the discharge means comprise an air filter and/or an activated carbon filter.

6. The aerosol exposure system according to claim 1, wherein the exposure chamber is an enclosure able to be hermetically closed.

7. The aerosol exposure system according to claim 2, comprising air supply means, disposed in the upper portion of the exposure chamber.

8. The aerosol exposure system according to claim 1, comprising means for controlling, and optionally adjusting, at least one parameter among the pressure, the temperature and the hygrometry inside the exposure chamber.

9. The aerosol exposure system according to claim 1, comprising means for maintaining a sample in the exposure chamber.

10. The aerosol exposure system according to claim 9, wherein the maintaining means are means for maintaining said sample in suspension in the exposure chamber.

11. The aerosol exposure system according to claim 1, wherein the aerosol product to be sprayed is a suspension of microorganisms.

12. The aerosol exposure system according to claim 1, wherein the aerosol product to be sprayed is a composition whose antimicrobial activity is to be tested.

13. A process for evaluating the integrity of a container comprising the successive steps of:
    (a) introducing the container to be evaluated into the exposure chamber of an aerosol exposure system comprising:
    an exposure chamber for receiving an aerosol product;
    a device for diffusing an aerosol product comprising a source of aerosol product to be sprayed, connected to an aerosol generator, said aerosol generator cooperating with a desiccator so as to at least partially eliminate the moisture from the aerosol product; and
    at least one supply duct bringing the aerosol product into the exposure chamber,
    wherein the aerosol product to be sprayed is a suspension of microorganisms;
    (b) generating an aerosol from the suspension of microorganisms, said aerosol being vaporized in the exposure chamber such that the microorganisms are in contact with the container;
    (c) recovering the container and optionally incubating the container under conditions allowing the growth of the microorganisms; and
    (d) detecting the possible presence of microorganisms inside the container.

14. The process according to claim 13, wherein the suspension of microorganisms is vaporized in the exposure chamber so as to obtain a concentration of microorganisms on the surface of the container between $10^4$ and $10^8$ CFU/cm$^2$.

15. A process for evaluating the antimicrobial activity of a product of interest comprising:
    (a) introducing microorganisms into the exposure chamber of an aerosol exposure system comprising:
    an exposure chamber for receiving an aerosol product;
    a device for diffusing an aerosol product comprising a source of aerosol product to be sprayed, connected to an aerosol generator, said aerosol generator cooperating with a desiccator so as to at least partially eliminate the moisture from the aerosol product; and
    at least one supply duct bringing the aerosol product into the exposure chamber,
    wherein the aerosol product to be sprayed is a suspension of microorganisms;
    (b) generating an aerosol from the product of interest, said aerosol being vaporized in the exposure chamber such that the microorganisms are in contact with said product of interest;
    (c) recovering the microorganisms; and
    (d) evaluating the rate of growth and/or survival of the microorganisms.

16. The aerosol exposure system according to claim 1, wherein the aerosol product to be sprayed is a suspension of spores.

* * * * *

UNITED STATES PATENT AND TRADEMARK OFFICE
CERTIFICATE OF CORRECTION

PATENT NO. : 11,466,304 B2
APPLICATION NO. : 16/965309
DATED : October 11, 2022
INVENTOR(S) : Alexandre Mura and Anja Fritsch It is certified that error appears in the above-identified patent and that said Letters Patent is hereby corrected as shown below:

In the Specification

Column 1,
Line 12, "28, 2019. 2019, which" should read --28, 2019, which--.

Signed and Sealed this
Fifteenth Day of August, 2023

Katherine Kelly Vidal
Director of the United States Patent and Trademark Office